United States Patent [19]
Buckley

[11] Patent Number: 6,086,609
[45] Date of Patent: Jul. 11, 2000

[54] CONTROLLED COLD THERAPY APPARATUS

[75] Inventor: John C. Buckley, Des Moines, Iowa

[73] Assignee: Jay R. Buckley, Des Moines, Iowa

[21] Appl. No.: 08/986,450

[22] Filed: Dec. 8, 1997

[51] Int. Cl.7 .................................................. A61F 7/00
[52] U.S. Cl. .......................... 607/104; 607/112; 607/114; 607/108
[58] Field of Search ...................... 607/96, 104, 108–112, 607/114; 165/46; 126/204

[56] References Cited

U.S. PATENT DOCUMENTS

| | | |
|---|---|---|
| D. 340,526 | 10/1993 | Molloy . |
| 2,272,481 | 2/1942 | Rinkes et al. . |
| 2,531,074 | 11/1950 | Miller . |
| 2,726,658 | 12/1955 | Chessey . |
| 3,186,404 | 6/1965 | Gardner . |
| 3,871,381 | 3/1975 | Roslonski . |
| 3,916,911 | 11/1975 | Sauder et al. . |
| 4,149,529 | 4/1979 | Copeland et al. . |
| 4,335,726 | 6/1982 | Kolstedt . |
| 4,459,468 | 7/1984 | Bailey ..................................... 607/104 |
| 4,856,294 | 8/1989 | Scaringe et al. . |
| 4,951,665 | 8/1990 | Schneider . |
| 4,964,402 | 10/1990 | Grim et al. . |
| 4,971,056 | 11/1990 | Seacord . |
| 5,086,771 | 2/1992 | Molloy . |
| 5,190,032 | 3/1993 | Zacoi ..................................... 607/104 |
| 5,507,792 | 4/1996 | Mason et al. ........................... 607/104 |
| 5,871,526 | 2/1999 | Gibbs et al. ............................ 607/104 |
| 5,888,185 | 3/1999 | Regan .................................... 607/104 |

OTHER PUBLICATIONS

Copy—(4–page) brochure dated 1995 by EBI Medical Systems entitled Answers To Your Questions About Templex™ Controlled Cold Therapy.
Copy—(4–page) brochure dated 1995—by EBI Medical Systems—entitled Controlled Cold Therapy.
Copy—(5–page) brochure dated 1996—by EBI Medical Systems, Inc.—entitled EBIce™ —New from EBI®: Compact, Cold Therapy.
Copy—2 page brochure by EBI Medical Systems dated Jun. 1996 and entitled EBIce Cold Therapy System Non–Sterile Pad 13"×15" . . .

Primary Examiner—Ryan Carter
Attorney, Agent, or Firm—Henderson & Sturm LLP

[57] ABSTRACT

A controlled cold therapy apparatus for treating body portions of an animal. The apparatus includes an appliance configured to fit over the body portion to be treated such that substantial total surface area contact is obtained between the body portion to be treated and the appliance. The appliance is comprised of a liquid impervious material which includes a liquid supply connector and a liquid return connector opened to internal flow channels to enable cooled liquid to be circulated through the appliance in a U-shaped flow pattern. The appliance is surrounded by an insulating jacket and is preferably secured around the body portion to be treated by hook and loop fastener strips. The apparatus further includes a liquid control station which circulates cooled liquid through the appliances connected thereto. The liquid control station may be a portable unit or a central fixture unit incorporated into a structure for treating multiple animals at the same time.

9 Claims, 8 Drawing Sheets

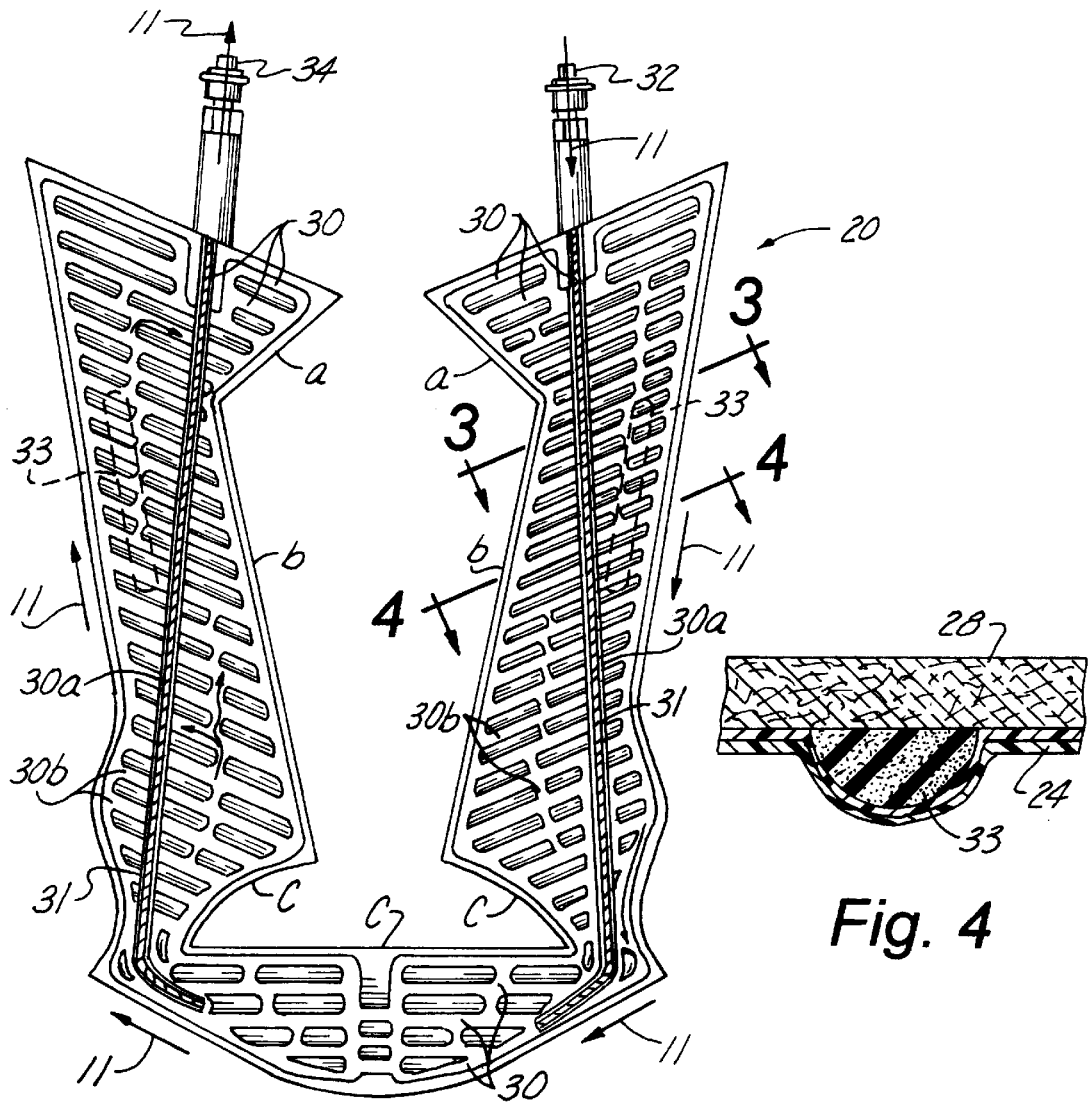
Fig. 2
Fig. 4
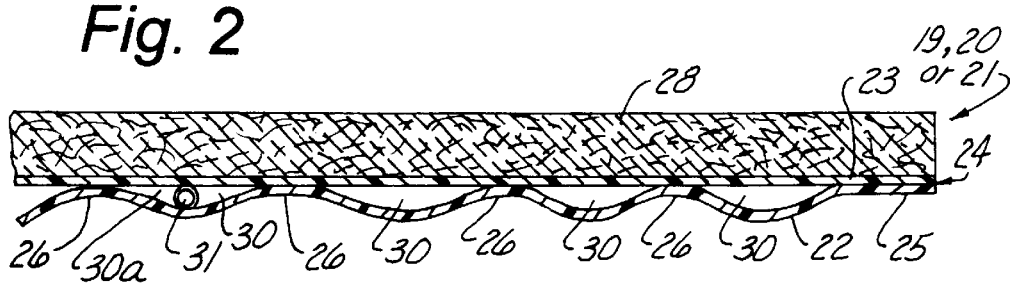
Fig. 3

CONTROLLED COLD THERAPY APPARATUS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

AUTHORIZATION PURSUANT TO 37 C.F.R. §1.71(d)(e)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office file or records, but otherwise reserves all copyright rights whatsoever.

BACKGROUND OF THE INVENTION

1. Technical Field

This invention relates generally to cold therapy treatment, and more particularly to an apparatus for circulating cold liquid around a body portion of an animal for localized cold therapy treatment.

2. Background Art

Localized cold therapy is routinely used in the treatment of injuries such as bruises, muscle strains, sprains and similar muscle, ligament and joint dysfunctions in humans particularly for injuries to feet, ankles, legs, arms or shoulders, and in the treatment of the legs and backs of animals such as horses, particularly the lower legs.

The conventional methods of applying such localized treatment to the body portions of animals, include immersing the body portion in an ice bucket or cold water bath or the application of cold wet cloths, ice bags, or more recently chemical ice packs. Such methods are incapable of providing a sustained treatment over a relatively long period of time and present numerous other disadvantages. It should be understood that although reference is often made to animals throughout this specification, such reference should be considered to include human beings.

The use of ice buckets, cold water baths or cold wet cloths is objectionable in that in the treatment of animals such methods cause the animals bedding and surroundings to become soaked with water. Also, such methods of treatment require the constant attention of an attendant to keep the animal, for example a horse, standing in the bucket or to continually change and re-wet the cloths. To a somewhat lesser, but still objectionable extent, continuous treatment with ice bags suffer from these same disadvantages. Ice packs and ice buckets have to be periodically replenished requiring personnel time and the expense of purchase, transport, storage and replacement of large quantities of ice. Also, the use of ice buckets, cold water baths, ice bags and wet cold cloths create a very damp cold which, while more tissue penetrating than dry cold, is usually a more painful procedure to the animal being treated.

The more recent introduction of chemical ice packs has solved some of these problems, but still present numerous disadvantages in the treatment of animals. Chemical ice packs are simply two or more chemical solutions or substances stored separately in a packet. Upon need, an internal seal is broken which allows the chemical solutions to mix. The mixing of the chemical solutions produces an endothermic reaction thereby cooling the cold pack to a predetermined low temperature. The cold chemical ice pack is then applied against and secured to the body portion to be treated by a wrapping. The disadvantages associated with the use of chemical ice packs are that the packs are expensive, the endothermic reaction lasts for only a short period of time, the packs cannot be reused, and the temperature of the pack cannot be adjusted. Additionally, the packs can rupture, thereby contaminating an animal's bedding or surroundings with toxic chemical solutions which can be harmful if the animal ingests the contaminated bedding.

To address the problems associated with ice buckets, cold water baths, cold wet cloths, ice packs, and chemical packs, numerous devices have been proposed for circulating a cooled fluid through an appliance which is applied to the body portion of the animal to be treated. Examples of such devices are disclosed in Saunder et al., U.S. Pat. No. 3,916,911; Roslonski, U.S. Pat. No. 3,871,381; and Copeland et al., U.S. Pat. No. 4,149,529.

By circulating a cooled fluid through a liquid appliance, the disadvantages of the above described conventional methods can be eliminated. For example, the appliance does not require replenishing since it is connected to a continuous flow of cooled liquid, the temperature can be adjusted, the animal's body part and bedding stays dry and constant attention by an attendant is not required.

Despite these advances in the use of cold therapy for the treatment of animals, there is still a need for a cold therapy apparatus which can be used to treat multiple body parts of an animal at the same time or multiple animals at the same time. Also, there is a need for a liquid appliance for use with a cold therapy apparatus that can be more securely fastened to the body portion of the animal and which provides substantially uniform surface contact between the appliance and the entire area of body portion to be treated. Additionally, there is a need for a cold therapy apparatus which may use potable water or non-toxic propylene glycol rather than a gas refrigerant or toxic antifreeze solution as disclosed in the above referenced patents. The use of potable water is desirable because it is readily available in most animal facilities and eliminates the potential for contamination of bedding with toxic refrigerants or antifreeze solutions in case of a rupture in the flexible conduits or appliances.

DISCLOSURE OF THE INVENTION

The present invention is directed to an apparatus for applying cold therapy to treat body portions of animals. It should be noted that any reference to animals should be considered to include human beings. The apparatus includes appliances configured to receive the body portions of the animal to be treated such that substantial total surface area contact is achieved between the appliance and the body portion. The appliances are comprised of a liquid impervious material which includes a liquid supply connector and a liquid return connector opened to internal flow channels to enable cooled liquid to be circulated through the appliance. The apparatus further includes a liquid control station having a liquid pump, a refrigeration system, a liquid cooling reservoir, a liquid temperature control, a liquid flow control, and at least one pair of liquid supply and liquid return ports.

The liquid supply and return ports of the control station are connected respectively to the liquid supply and return connectors of the appliance by flexible conduits. The liquid control station can be powered by an internal combustion engine and generator or the liquid control station can be electrically powered.

The supply and return ports of the liquid control station may be equipped with a manifold device thereby enabling more than one appliance to be connected to the control station at one time.

The liquid control station may be a portable unit or a central fixture unit installed in a structure for treating multiple animals at the same time. With a central control station, a network of piping comprising supply and return pipes is routed throughout the structure with quick-disconnect couplers installed in each stall. The network of supply and return pipes terminate into a single supply pipe and return pipe which are then connected to the central control station. Numerous cold therapy appliances in each stall can then be connected to this network of piping by flexible conduits thereby enabling multiple animals to be treated at one time.

To enable multiple appliances to connect to a single control station, a variable speed or variable pressure liquid pump is required to ensure constant uniform flow and pressure to each appliance connected to the system. It should be understood that as more appliances are connected to the control station, more liquid must be circulated through the system and as appliances are removed from the system, less liquid must be circulated through the system, thus changing the pressure and volume requirements of the pump.

Other objects, advantages, and novel features of the present invention will become apparent from the following detailed description of the invention when considered in conjunction with the accompanying drawings.

BRIEF DESCRIPTION OF THE DRAWINGS

FIG. 2 shows a detailed flat layout view of the sealed envelope of a cold therapy appliance for a horses rear leg;

FIG. 3 shows a sectional view of the cold therapy appliance taken along lines 3—3 of FIG. 2;

FIG. 4 is another sectional view of the cold therapy appliance taken along lines 4—4 of FIG. 2;

BEST MODE FOR CARRYING OUT THE INVENTION

Figure 1:
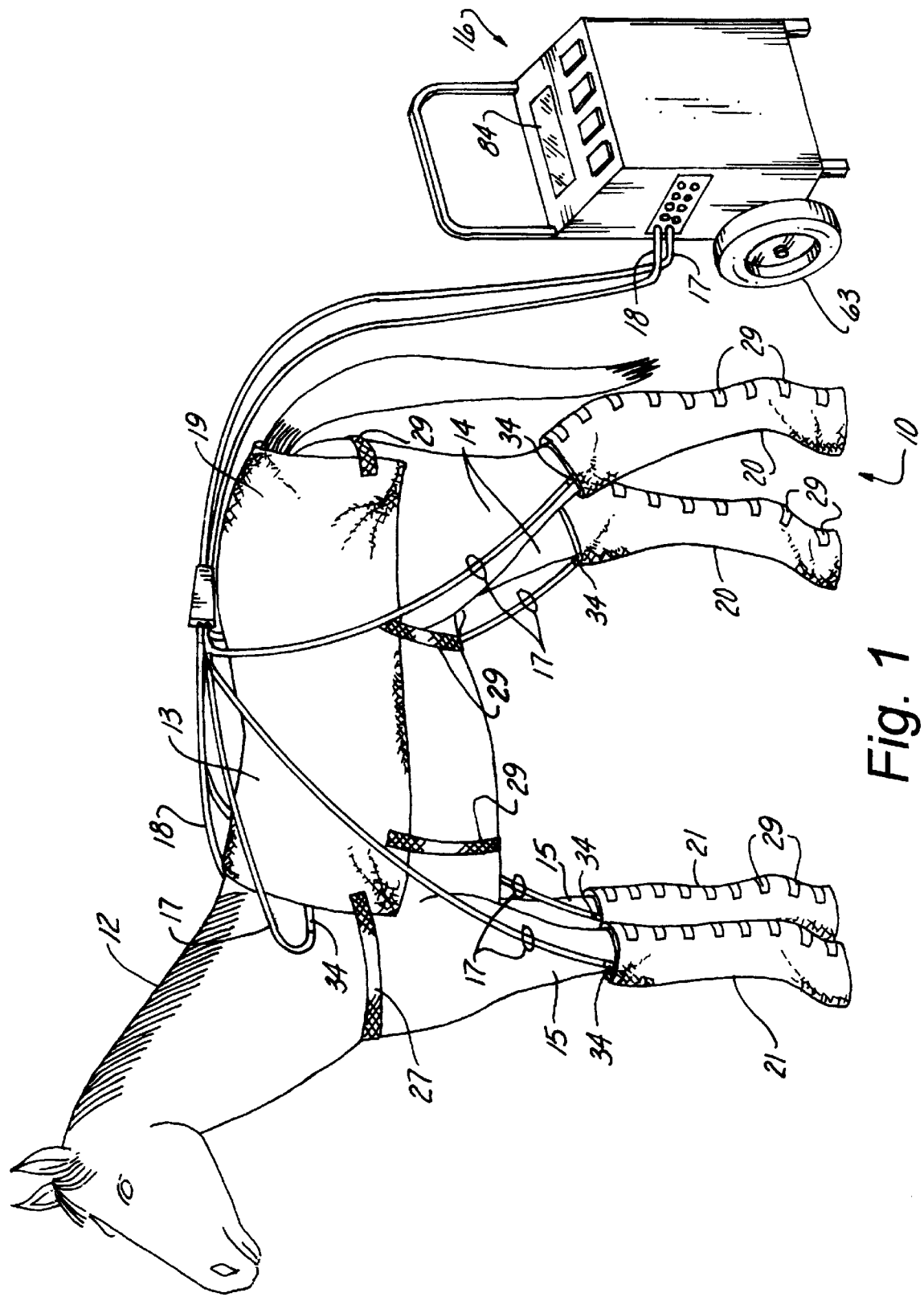
FIG. 1 shows the cold therapy apparatus of the present invention being used to treat the front legs, rear legs and back of a horse.

Referring now to the drawings wherein like reference numerals designate identical or corresponding parts throughout the several views, FIG. 1 shows the cold therapy apparatus (10) of the present invention being used to treat body parts (13, 14 and 15), for example, of a horse (12). Although the present invention is described and illustrated below as being particularly designed for the treatment of horse's legs and back, it should be understood that the apparatus (10) can be adapted for the treatment of other body parts of various animals including humans. Therefore the scope of this invention should not be considered as limited in the treatment of horse's.

The apparatus (10) includes a portable liquid control station (16) which connects to an appliance (19, 20 or 21) by a pair of insulated, flexible, liquid supply and return conduits (18 and 17 respectfully) preferably ⅜ to ½ inch in diameter. The appliance (19, 20 or 21) is configured for the body portion of the animal to be treated in a manner which provides substantially total surface contact. As shown in FIG. 1, the appliance (19, 20 or 21) may be configured to receive the back (13) of a horse (12) which encompasses the withers, the back, the loin, and the croup or alternatively the lower rear leg (14) of a horse (12) which encompasses the hock, cannon, ankle, pasterns and hoof, or alternatively, the lower front leg (15) of a horse (12) which encompasses the knee, cannon, ankle, pasterns and hoof.

Figure 5:
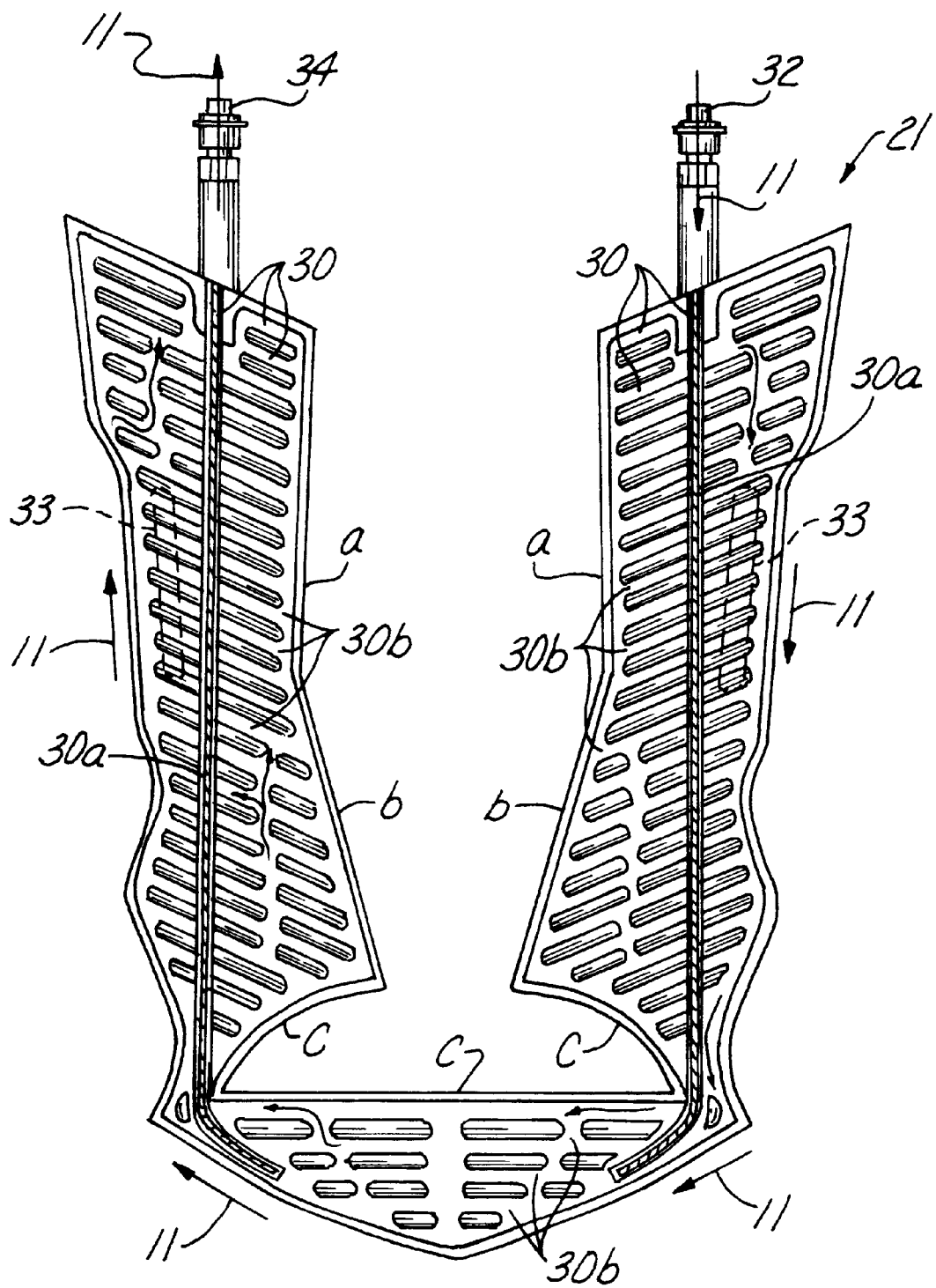
FIG. 5 shows a detailed flat layout view of the sealed envelope of a cold therapy appliance for a horses front leg.
Figure 6:
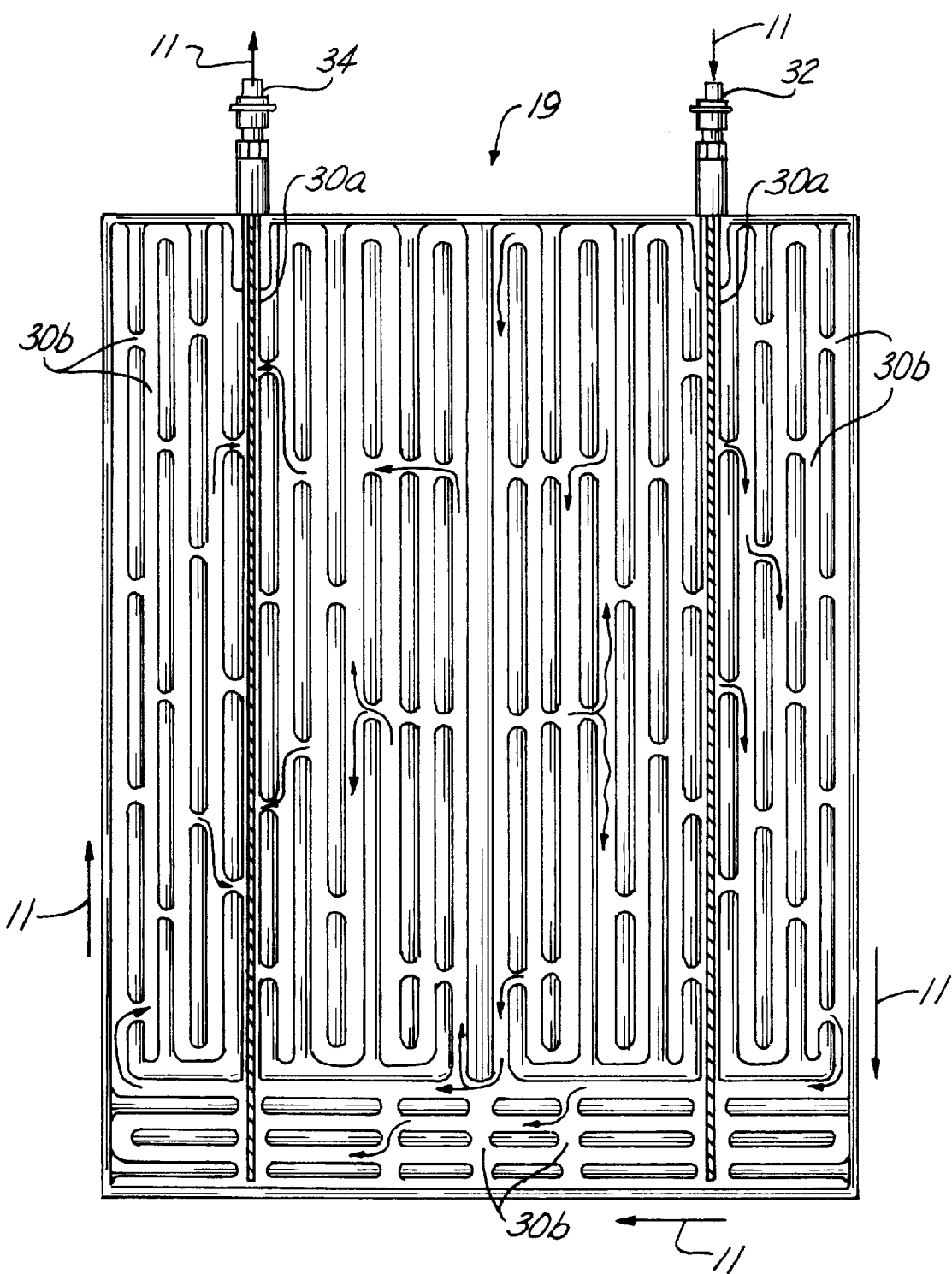
FIG. 6 shows a detailed flat layout view of the sealed envelope of a cold therapy appliance for a horses back.

FIGS. 2 and 5 are flat layout views of the front and rear leg appliances (21 and 20) respectively. FIG. 6 is a layout view of the appliance (19) for treatment of the horse's back (13). These figures will be discussed in further detail later.

As best illustrated in FIG. 3, which is a cross-sectional view taken along lines 3—3 of the rear leg appliance (20) of FIG. 2, but is typical of all appliances (19, 20 and 21), the appliance is comprised of an inner wall (22) and outer wall (23). The walls (22 and 23) are constructed out of a water-impervious, synthetic, rubberized, polymeric material capable of remaining flexible and resilient at temperatures between 0 degrees Fahrenheit and 32 degrees Fahrenheit. The thickness of the walls (22 and 23) is not critical, though a thickness of about 4 mils to about 15 mils is preferred. The walls (22 and 23) are die-stamped or heat stamped together thus creating a single unitary sealed envelope (24) having a periphery seal (25) and a series of internal seals (26) thereby forming internal flow channels (30) between the two walls (22 and 23). The envelope (24) is bonded to an insulating jacket (28) thereby creating a single unitary insulated appliance (19, 20 or 21).

The insulating jacket (28) is preferably a closed cell synthetic polymeric foam. Other insulating materials such as open cell polymeric foams and fibrous composites may also be used. An insulating jacket thickness of about 100 mils to about 250 mils is preferred for optimum insulation and pad flexibility. An additional outside layer of washable, durable fabric such as nylon or Kevlar® may be used to protect the insulating jacket from wear or from being soiled.

As shown in FIG. 4, disposed between the outer wall (23) and the insulating jacket (28) are positioned a pair of conforming members (33), preferably constructed out of a polyurethane foam. The conforming members (33) are disposed in the appliances (20 and 21) between the outer wall (23) and the insulating jacket (28). These conforming members (33) act to conform the appliances (20 and 21) to the areas of concavity of the legs (14 and 15) between the cannon bone and the tendons to ensure substantial surface area contact of the appliance (20 and 21) with the legs (14 and 15).

Referring now to FIGS. 2, 5 and 6, in viewing the internal flow channels (30) of the respective appliances (19, 20, or 21), it should be appreciated that the flow channels (30) include larger main flow channels (30a) which branch throughout the appliance into a series of smaller branch channels (30b). These main channels (30a) and (30b) cover the entire surface area of the appliance. It should be appreciated that the appliances (19, 20 or 21) have a generally U-shaped flow configuration as illustrated by the arrows (11). A supply connector (32) and an return connector (34) in communication with the internal flow channels (30) are positioned on opposite sides of the U-Shaped flow configuration thus requiring the cooled liquid to enter the appliance (19, 20 or 21) through the supply connector (32) on one side and circulate through the entire U-shaped flow channel (30) before exiting through the return connector (34) on the other side of the appliance (19, 20 or 21).

It has been determined that the flow channels (30) may collapse due to the suction force of the liquid pump (discussed later), thereby preventing the cooling solution from dispersing throughout the internal flow channels (30) of the appliance (19, 20 or 21). To overcome this problem, spiral tubes (31) (see e.g., FIG. 3) are placed in the main flow channels (30a) to prevent them from collapsing. If the main flow channels (30a) cannot collapse, the cooled liquid will be able to circulate throughout the appliance do to the many alternate branch channels (30b).

Figure 7:
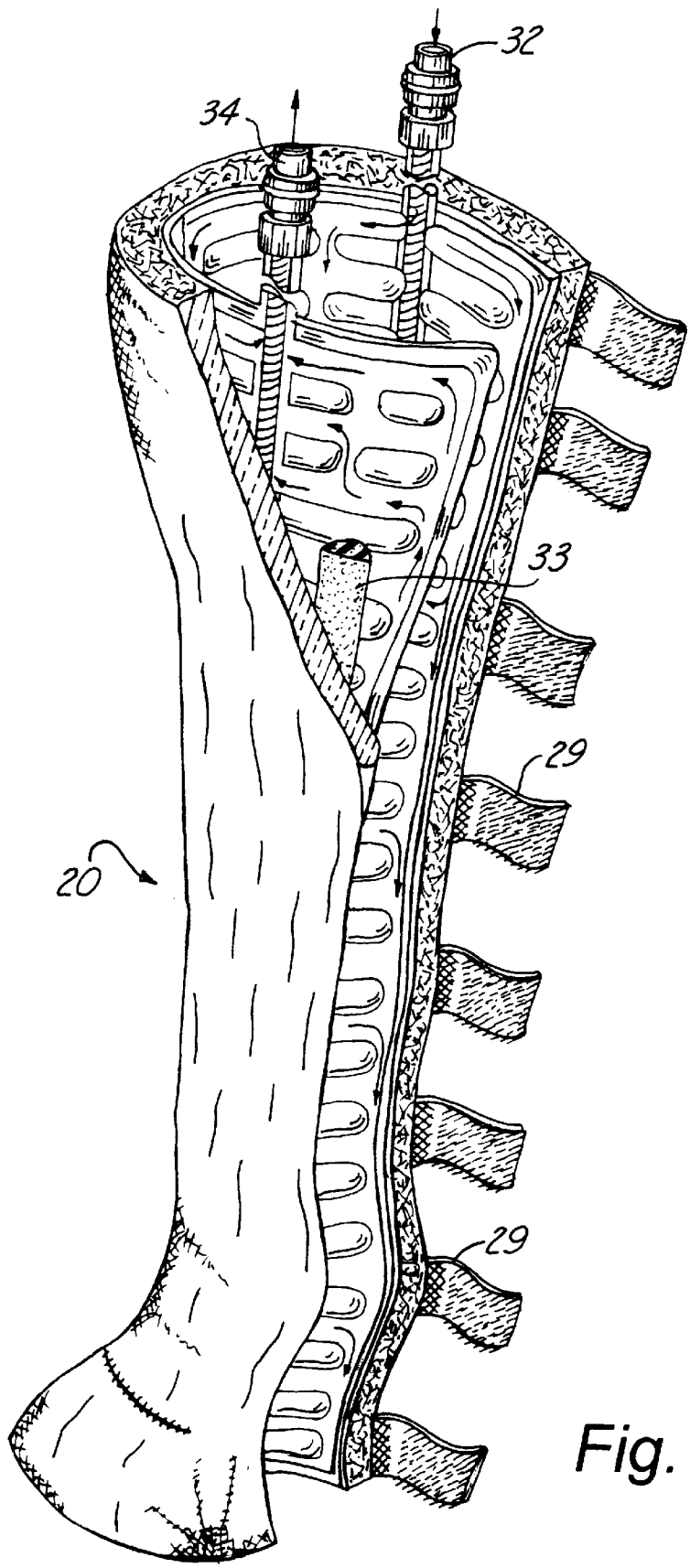
FIG. 7 is a perspective view of a configured cold therapy appliance for a horses rear leg.

The appliances (19, 20 and 21) are secured to the body portion to be treated by fasteners (29) (see FIGS. 1 and 7). The fasteners are preferably hook-type strips (29) (commonly referred to as Velcro® strips). When the appliance (19, 20 or 21) is wrapped around the body portion to be treated, the hook fastener strips (29) are pulled and attached to the opposite side of the exterior of the insulating jacket (28) to secure the appliance (19, 20 or 21) firmly in place. It should be appreciated that if the exterior surface of the insulating jacket (28) is of a type of material to which the hook-type fasteners (29) will not readily attach, loop-type strips (not shown) may have to be secured to the insulating jacket (28) for the hook fasteners (29) to attach to.

As mentioned previously, FIGS. 2 and 5 are flat layout views of the front and rear leg appliances (20 and 21) respectively. In order to construct the appliances (20 and 21) from flat material, so that there is substantially complete surface area contact between the cooling surface of the appliance and the body portion to be treated, the envelope (24) and insulating jacket (28) must have the general shape as shown in FIG. 2 or 5. It is desirable to construct the appliances from flat material so that the envelope (24) can be die stamped or heat stamped as discussed above to create the internal flow channels (30) from two separate layers (22 and 23). Once the envelope (24) and insulating jacket (28) are fitted and bonded together, the edges a—a, b—b, and c—c (FIGS. 2 and 5) are secured together by glue or stitching or both. The assembled appliance (20 or 21) will then have the 3-dimensional configuration of the respective body portion to be treated, for example as shown in FIG. 7.

Figure 8:
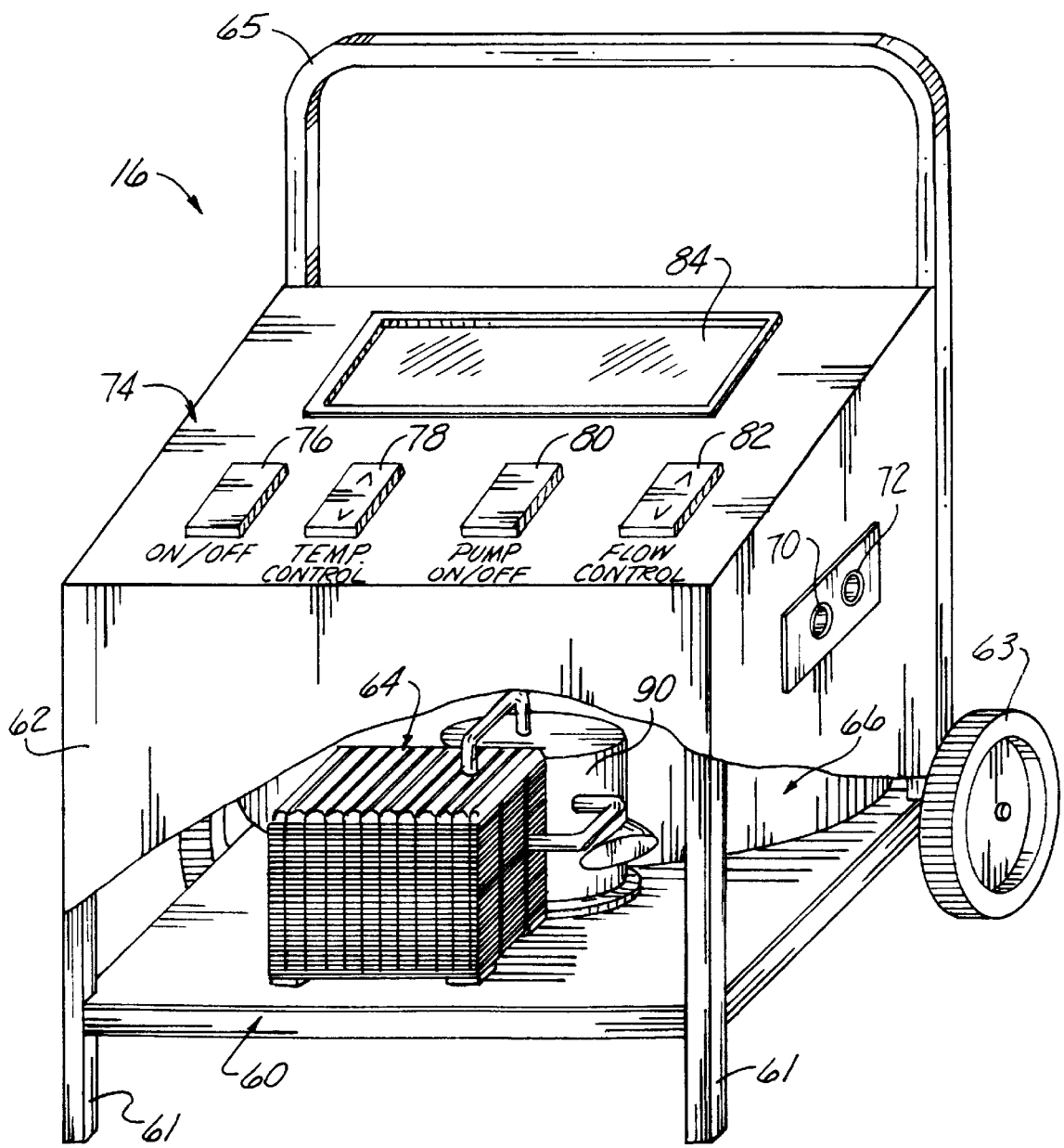
FIG. 8 shows a portable liquid control station.

Referring now to FIG. 8, the portable liquid control station (16) comprises a main frame (60) surrounded by a housing (62). Attached to the bottom of the housing are a pair of pneumatic rear wheels (63) and front legs (61). A handle (65) is mounted to the main frame (60) to allow the station (16) to be transported and positioned in close proximity to the animal to be treated by tilting the appliance so it can be wheeled much like a two-wheeled dolly cart. It should be appreciated that a pair of front wheels could replace the front legs (61) resulting in a four-wheeled cart.

Figure 11:
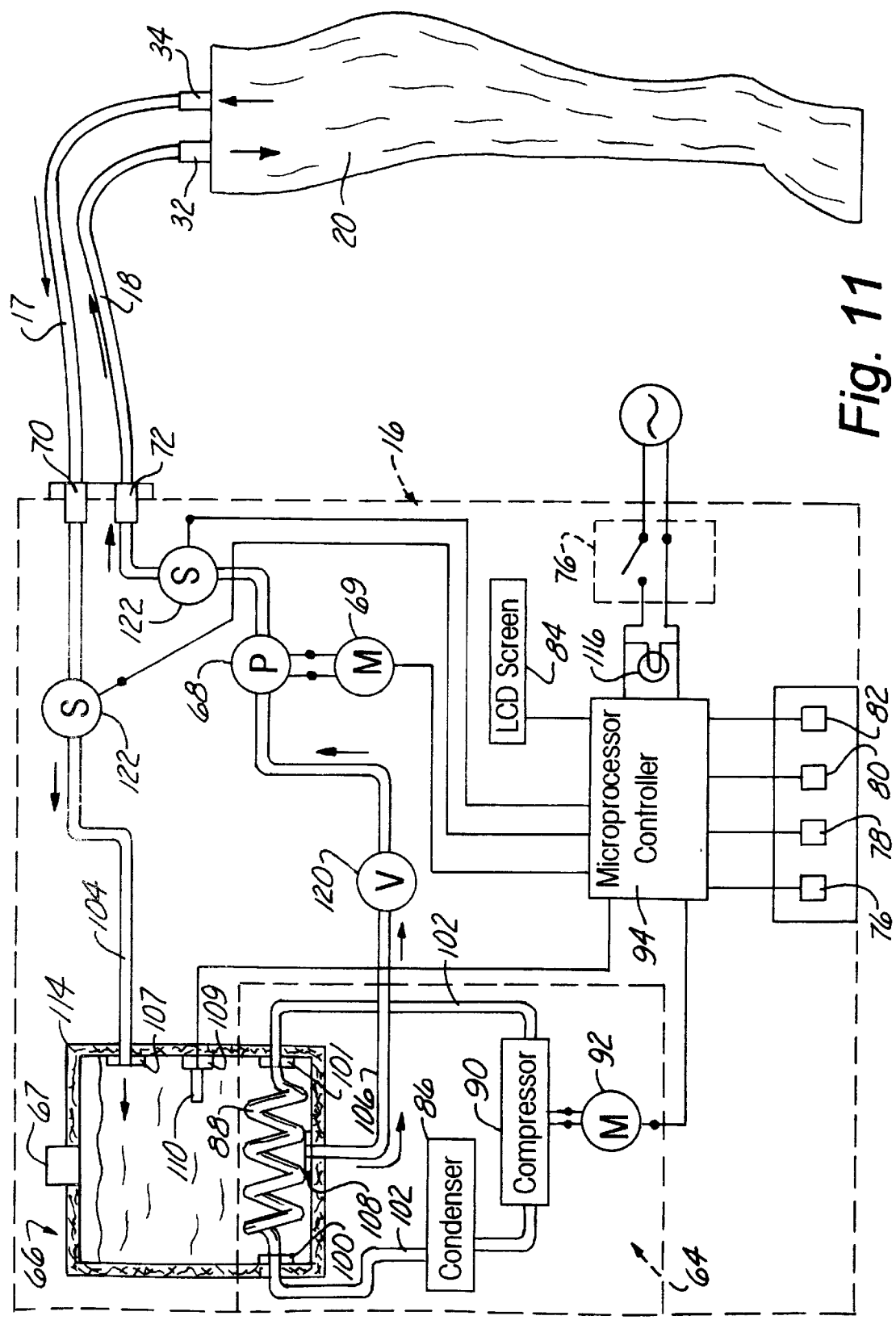
FIG. 11 is a schematic diagram of the cold therapy apparatus of the present invention.

Many of the elements of the control station (16) are hidden in FIG. 8 and are schematically illustrated in FIG. 11.

The station (16) contains a refrigeration system (64), a liquid cooling reservoir (66), a liquid pump (68), a liquid pump motor (69), a supply port (72) and an return port (70) projecting through the side of the housing (62). A control panel (74) located on the top of the housing (62) includes a main power on/off switch (76), a temperature controller (78), a pump on/off switch (80), a flow or pressure controller (82) and a liquid crystal display (LCD) screen (84). Electrical power for operating the control station (16) is preferably supplied by an external 120 volt AC power source but electrical power could also be supplied by an internal combustion engine operating an electric generator.

The refrigeration system (64) includes a condenser (86), evaporator coils (88) disposed in the bottom of the liquid reservoir (66), a compressor (90), and a compressor motor (92).

The liquid reservoir (66) is a tank preferably having a five gallon capacity and constructed of polymeric material such as polyethylene. A sleeve (67) is provided near the top of the tank for filling the liquid reservoir with the liquid to be circulated through the system. It is preferred to use potable water in the system because it is readily available in most animal facilities and it is non-toxic in the case of spills or rupture of the appliance (19, 20 or 21) or return and supply conduits (17 and 18). Non-toxic propylene glycol may also be mixed with the water if temperatures below freezing are desired for treatment. Liquid tight fittings (100, 101) are required for the passage of the refrigerant tubing (102) between evaporation coils (88) and compressor (90) and condenser (86). Supply and return piping (106 and 104 respectively) are coupled to the reservoir (66) also by liquid tight fittings (107 and 108) on the tank wall and bottom respectively. Additional liquid tight fittings (109) are required for the tank thermal sensors (110) (discussed below). Thermal insulation (114) in blanket or spray-on form is used to surround the liquid reservoir (66) to increase thermal efficiency.

The liquid circuit includes a supply line (106), preferably constructed out of flexible, synthetic, reinforced rubber, in communication with the liquid reservoir tank (66). A liquid pump (68) is connected to the supply line (106). The pump is operated by the pump motor (69). Intermediate the reservoir tank (66) and pump (68) is a one way check valve (120) to prevent back-flow of the cooled liquid into the reservoir (66). The supply line (106) terminates with a quick disconnect coupler at the supply port (72). The appliance supply conduit (18) is coupled at one end to the supply port (72) of the control station (16) and at its other end to the supply connector (32) of the appliance (19, 20 or 21). The appliance return conduit (17) is coupled at one end to the return connector (34) of the appliance (19, 20 or 21) and at its other end to a quick disconnect coupler at the return port (70) of the control station (16). A return line (104), preferably constructed out of flexible synthetic reinforced rubber, in communication with the reservoir tank (66) and return port (70) returns the used water from the appliance (19, 20 or 21) to the reservoir tank (66).

The temperature controller (78) is used to set the desired temperature for the liquid in the reservoir (66). A thermal sensor (110) is disposed in the reservoir (66) to monitor the temperature of the liquid. The thermal sensor (110) is electrically coupled to a microprocessor controller (94) which controls the compressor motor (92). The temperature controller (78) and LCD screen (84) are likewise coupled to the microprocessor (94) so the user can view the temperature settings and actual temperatures. The necessary mechanical and electrical components and wiring required for controlling a refrigeration system and displaying the temperature on a LCD screen is well known by one skilled in the art and is not considered part of this invention. Therefore, the schematic of FIG. 11 is used for general illustration purposes only.

The flow or pressure controller (82) is used to set the desired flow rate of the cooled liquid through the liquid circuit. The preferred flow rate is between two to four gallons per minute (2–4 gpm). The flow controller (82) is also electrically coupled to the microprocessor controller (94) which is in turn electrically coupled to pressure sensors (122) and the LCD screen (84). The pressure sensors (122) are disposed between the liquid pump (68) and the supply port (72) on the supply line (106), and the return port (70) and the reservoir (66) on the return line (104). If the pressure exceeds or falls below a predetermined pressure, the microprocessor controller (94) will shut down the pump motor (69) and set off an alarm condition. The necessary mechanical and electrical components and wiring required for monitoring and controlling pump operation, line pressure, and displaying the pressure or flow rate on a LCD screen is well known by one skilled in the art and is not considered part of this invention. Therefore, the schematic of FIG. 11 is used for general illustration purposes only.

In operation, the appliance (19, 20 or 21) is secured to the body portion of the animal to be treated by the fastener strips (29). Flexible return and supply conduits (17 and 18) are connected to the respective connectors (32 and 34) on the appliance (19, 20 or 21) and ports (70 and 72) on the liquid control station (16). The liquid reservoir (66) is filled with potable water or the propylene glycol solution as previously discussed. The main power switch (76) of the control station (16) is switched to the on position. The main power lamp (116) lights signifying the liquid control station (16) is in operation. The microprocessor controller (94) monitors the temperature setting and the temperature of the liquid in the reservoir (66). If the liquid is warmer than the desired temperature setting, the microprocessor controller (94) will activate the compressor motor (92) which circulates the refrigerant through the condenser (86) and evaporator coils (88) thereby cooling the solution in the liquid reservoir (66). When the desired liquid temperature is reached as displayed on the LCD screen (84), the microprocessor controller (94) activates the liquid pump motor (69). The cooled water solution is drawn through the supply line (106) and the check valve (120). The cooled solution, then travels through the supply port (72) into the supply conduit (18). The cooled solution enters the appliance (19, 20 of 21) through the supply connector (32). The cooled water is circulated through the flow channels (30) and exits the appliance (19, 20 or 21) through the return connector (34). The water is forced through the return conduit (17) into the return port (70) of the liquid control station (16) and returns to the liquid reservoir (66) via the return line (104) where it is chilled and recirculated.

Figure 9:
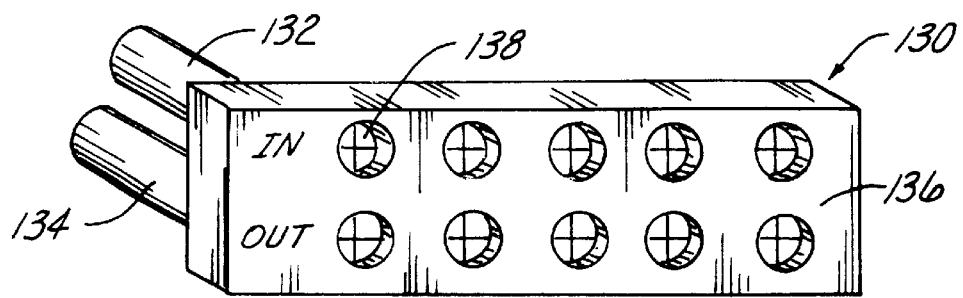
FIG. 9 shows a manifold device for connecting multiple appliances to a single liquid control station.

The supply and return ports (72 and 70) of the liquid control station (16) may be equipped with a manifold device (130) (FIG. 9) to enable more than one pair of return and supply conduits (17 and 18) to be connected to the liquid circuit thereby enabling more than one appliance (19, 20 or 21) to be connected to the control station (16) at one time. The manifold device (130) includes two nipples (132 and 134) that are adapted to be inserted into the return and supply ports (70 and 72) in the control station (16). A hollow manifold chamber (136) having a plurality of even numbered apertures (138) spaced along its length are adapted to receive the return and supply conduits (17 and 18) of multiple appliances (19, 20 and 21). FIG. 9 illustrates a manifold device (130) capable of receiving five pairs of return and supply conduits (17 and 18) from five appliances (19, 20 or 21). It should be understood that the manifold device (130) depicted in FIG. 9 is for illustration purposes only and that a manifold device having more or fewer apertures (138) can be constructed.

It should also be understood, that to enable multiple appliances (19, 20 or 21) to connect to a single control station (16), a variable speed or variable pressure liquid pump (68) is required to ensure constant uniform flow and pressure to each appliance (19, 20 or 21) connected to the system. It should be appreciated that as more appliances (19, 20 or 21) are connected to the control station (16), more liquid must be circulated through the system. Likewise, as appliances (19, 20 or 21) are removed from the system, less liquid must be circulated through the system, thus changing the flow and pressure requirements of the pump (68).

Figure 10:
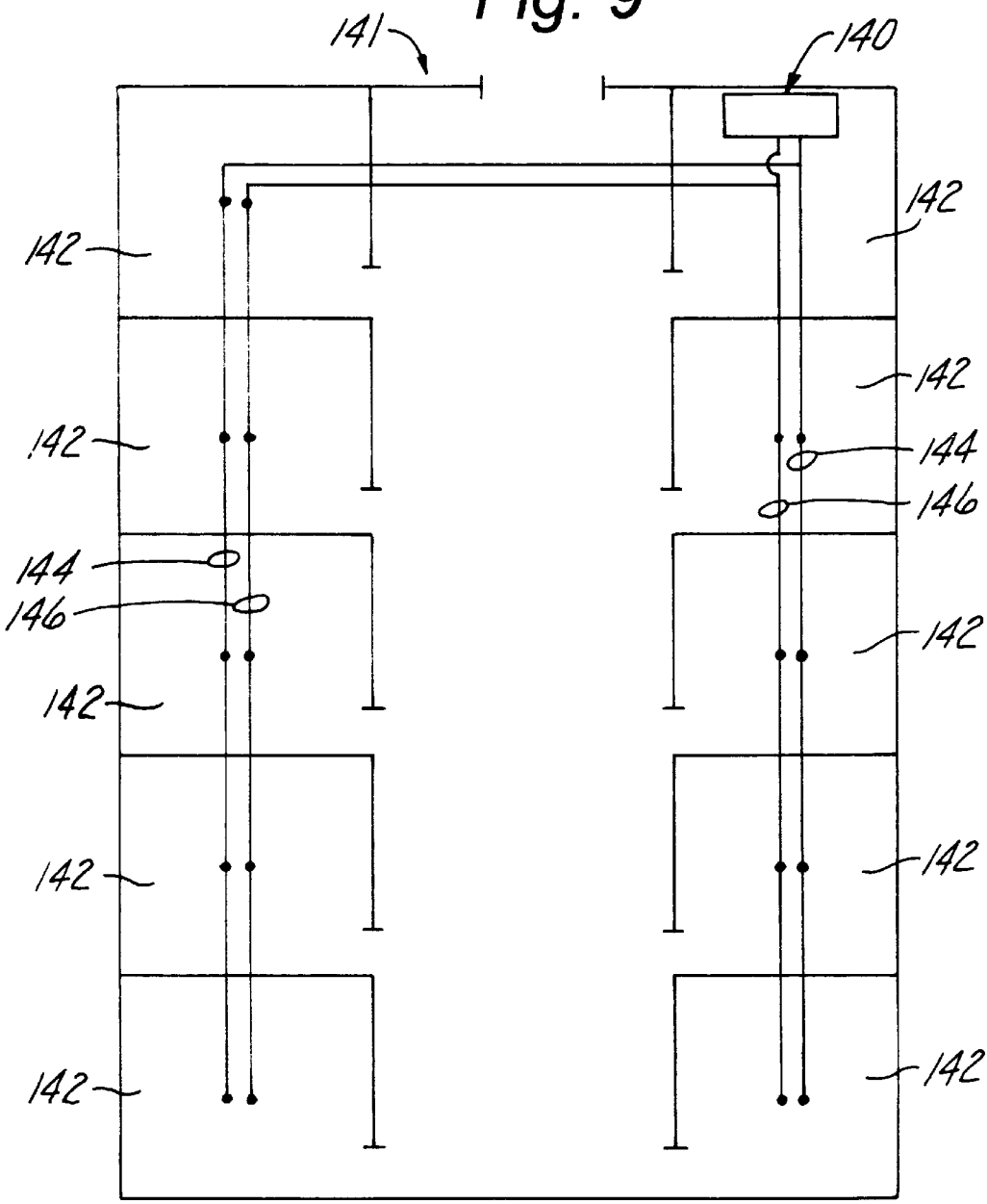
FIG. 10 is a plan view of a structure showing multiple stalls connected to a central liquid control station by piping for treating multiple animals at one time.

Another embodiment of the cold therapy apparatus (10) is shown in FIG. 10. Rather than having a portable liquid control station (16), a central liquid control station (140) is used in a multi-stall barn (141), much like a central air conditioner in a building. In this embodiment, each stall (142) has access to a network of return and supply piping (144 and 146) for attaching at least one cold therapy appliance (19, 20 or 21). Thus, multiple horses in separate stalls (142) can be treated at one time. The network of return and supply pipes (144 and 146) terminate into a single return pipe and supply pipe which are then connected to the central control station (140). The central control station (140) is similar to the portable control station (16) described above, except that a larger cooling reservoir (66), refrigeration system (64), and higher volume liquid pump (68) may be required depending on the number of animals and appliances (19, 20 or 21) expected to be used at one time.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

What is claimed is:

1. A controlled cold therapy apparatus for applying cold therapy to the back and leg portions of a horse, comprising:
   (a) a plurality of liquid appliances configured to receive the back and leg portions, respectively, of a horse to be treated wherein each of said liquid appliances includes:
      (i) a sealed envelope having an inside wall and an outside wall, said envelope being comprised of a flexible liquid-impervious material divided into flow channels, wherein said flow channels direct liquid in a substantial U-shaped flow pattern, and wherein said envelope includes a liquid supply connector in communication with one side of said U-shaped flow pattern and a liquid return connector in communication with one other side of said U-shaped flow pattern;
      (ii) an insulating jacket having an inside surface and an outside surface, wherein said inside surface of said insulating jacket is bonded to said outside wall of said envelope; and
      (iii) fasteners for securing each appliance around the selected body portion to be treated;
   (b) a liquid control station for cooling and pumping a liquid solution through a liquid circuit; and (c) flexible return and supply conduits for coupling said appliances to said liquid control station comprising said liquid circuit, and wherein the selected liquid appliances configured to receive the leg portions of the horse are further provided with conforming members disposed between said outside wall and said insulating jacket; wherein said conforming members are positioned to conform said selected liquid appliances to concavities of said leg portions to be treated.

2. The controlled cold therapy apparatus as in claim 1, wherein said selected liquid appliances have a three dimensional configuration of the leg portion to be treated.

3. The controlled cold therapy apparatus of claim 1, wherein said liquid appliances further includes at least one tube disposed in at least one of said flow channels to prevent collapsing of said flow channels.

4. The controlled cold therapy apparatus of claim 1, wherein said liquid control station comprises:

(a) a liquid pump;

(b) a refrigeration system;

(c) a liquid temperature control;

(d) a liquid flow control;

(d) at least one pair of liquid supply and liquid return ports; and (e) a liquid cooling reservoir.

5. The controlled cold therapy apparatus of claim 4, wherein said liquid control station is a portable unit.

6. The controlled cold therapy apparatus of claim 5, wherein said liquid control station includes a manifold device coupled to said liquid supply port and said liquid return port to enable more than one pair of return and supply conduits to be connected to the liquid control station.

7. The controlled cold therapy apparatus of claim 4, wherein said liquid control station is a central liquid control unit fixture installed in a structure.

8. The controlled cold therapy apparatus of claim 7, wherein said structure includes a plurality of stalls with a network of supply piping and a return piping, said supply and return piping including supply and return conduit couplers in each of said plurality of stalls.

9. The controlled cold therapy apparatus of claim 8, wherein said stalls each include a manifold device coupled to said liquid supply pipes and said liquid return pipes to enable more than one appliance to be connected to said piping in each stall at the same time.

* * * * *